United States Patent [19]

Schmidt et al.

[11] Patent Number: 5,130,466
[45] Date of Patent: Jul. 14, 1992

[54] DIISOCYANATE, A PROCESS FOR ITS PRODUCTION AND ITS USE

[75] Inventors: Manfred Schmidt, Dormagen; Klaus König, Odenthal; Peter Heitkämper, Dormagen; Josef Pedain, Cologne, all of Fed. Rep. of Germany

[73] Assignee: Bayer Aktiengesellschaft, Bayerwerk, Fed. Rep. of Germany

[21] Appl. No.: 463,713

[22] Filed: Jan. 11, 1990

Related U.S. Application Data

[63] Continuation of Ser. No. 103,081, Sep. 30, 1987, abandoned.

[30] Foreign Application Priority Data

Oct. 3, 1986 [DE] Fed. Rep. of Germany ....... 3633712

[51] Int. Cl.$^5$ .............................. C07C 69/00
[52] U.S. Cl. .................................... 560/129
[58] Field of Search ......................... 560/129

[56] References Cited

U.S. PATENT DOCUMENTS 3,567,763 3/1971 Emmons et al.

FOREIGN PATENT DOCUMENTS 1251718 10/1971 United Kingdom .

OTHER PUBLICATIONS

H. Ulrich et al, Liebigs Ann. Chemie, 1975, pp. 1317-1321.

Primary Examiner—Alan Siegel
Attorney, Agent, or Firm—Joseph C. Gil; Thomas W. Roy

[57] ABSTRACT

The present invention is directed to a diisocyanate which corresponds to the formula

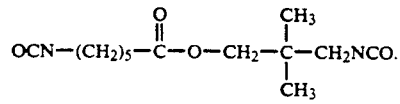

The present invention is also directed to the preparation of this diisocyanate and to its use for the production of polyisocyanate polyaddition products.

2 Claims, No Drawings

DIISOCYANATE, A PROCESS FOR ITS PRODUCTION AND ITS USE

This application is a continuation, of application Ser. No. 07/103,081 filed Sep. 30, 1987 now abandoned.

BACKGROUND OF THE INVENTION

1. Field of the Invention

This invention relates to a new aliphatic ester diisocyanate, to a process for its production and to its use in the production of plastics by the isocyanate polyaddition process.

2. Description of the Prior Art

Diisocyanates containing ester groups are known. Compounds of this type are described, for example, in DE-OS 1,618,798. The ester diisocyanates are produced by esterification of aminocarboxylic acids with certain alkanolamines and reaction of the resulting ester diamines or their hydrochlorides with phosgene. The aminocarboxylic acid used in this process may be, for example, 6-aminocaproic acid which is inexpensively obtainable from ε-caprolactam. However, DE-OS 1,618,798 itself shows that the use of the alkanolamines mentioned therein is accompanied by certain disadvantages. Additional difficulties were encountered in the reproduction of Examples 7 and 8 of DE-OS 1,618,798 (see following Comparison Examples 1 and 2). Thus, the dihydrochlorides prepared from the alkanolamines mentioned as preferred accumulate in the form of pasty, solid-liquid mixtures which are insoluble in the usual organic solvents. Isolation, for example by careful removal of the solvent, leads to further decomposition of the products. It follows from this that purity testing of the dihydrochlorides is not possible and that, in particular, any purification necessary cannot be carried out. A modified procedure for the production of the dihydrochlorides using 6-aminocaproyl chloride hydrochloride as starting material, for example according to H. Ulrich et al, Liebigs Ann. der Chemie, 1975, page 1317, does not produce any improvement. In this process also, the reaction products with the alkanolamines mentioned as preferred in DE-OS 1,618,798 are obtained as greasy products which cannot be worked up or purified (see following Comparison Example 3) and, therefore, cannot be reacted to give pure diisocyanates. Due to the thermal instability of the dihydrochlorides, the exchange for the solvent required for phosgenation is also very difficult.

The phosgenation in o-dichlorobenzene described in Example 8 of DE-OS 1,618,798 is not carried out in the usual way under reflux conditions, so that isocyanates having high contents of bound chlorine are obtained, as also mentioned in this Example.

However, when phosgenation is carried out under reflux conditions, even the use of a low-boiling solvent (see Comparison Example 3 below) fails to give useful yields or pure products because the thermal instability makes purification impossible. If, by contrast, phosgenation is carried out under reflux in o-dichloro-benzene, it only leads to decomposition products and not to significant yields of isocyanate.

These disadvantages would appear to be the reason why the diisocyanates specifically described in DE-OS 1,618,798 have not yet acquired any commercial significance.

An object of the present invention is to provide a new diisocyanate containing ester groups wherein its production is not attended by any of the above-described disadvantages, i.e., which is readily obtainable in high yields from inexpensive starting materials and which by virtue of its properties is eminently suitable as an isocyanate component in the production of polyisocyanate polyaddition products, preferably polyurethane plastics. This object may be achieved in accordance with the present invention.

SUMMARY OF THE INVENTION

The present invention is directed to a diisocyanate which corresponds to the formula

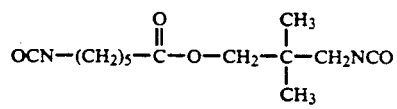

The present invention is also directed to a process for the production of this diisocyanate which is characterized in that a diamine dihydrochloride corresponding to the following formula

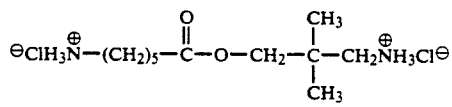

is reacted with phosgene.

Finally, the present invention also relates to the use of the diisocyanate according to the invention, optionally blocked by blocking agents for isocyanate groups, as an isocyanate component for the production of plastics by the isocyanate polyaddition process.

DETAILED DESCRIPTION OF THE INVENTION

The diisocyanate according to the invention has significant advantages over the diisocyanates containing ester groups which are known from DE-OS 1,618,798, particularly with regard to its preparation. Thus, the use of neopentanol-amine (3-amine-2,2-dimethylpropanol) or its hydrochloride as reactant for 6-aminocaproyl chloride hydrochloride leads to the dihydrochloride to be used in the process according to the invention in substantially analytically pure form (see Example 4 below). By virtue of its crystalline consistency, the starting material according to the invention is easy to handle and to further process.

In particular, by virtue of its thermal stability, the dihydrochloride may readily be phosgenated under reflux conditions in the solvents normally used for phosgenation such as chlorobenzene or o-dichlorobenzene. This phosgenation in chlorobenzene or o-chlorobenzene, which preferably takes place under reflux conditions at normal pressure, is generally carried out by continuously introducing phosgene into a suspension of the dihydrochloride under reflux until a clear solution is formed. The reaction mixture is then freed from excess phosgene and from chlorobenzene by distillation. The diisocyanate according to the invention accumulates as distillation residue and may be worked up by vacuum distillation (see Example 5 below).

The diisocyanate according to the invention is a valuable starting material for the production of isocyanate-based plastics, preferably polyurethanes, by reaction with compounds having isocyanate reactive groups, preferably hydroxyl groups, in accordance with the isocyanate-polyaddition process. To this end, the diisocyanate may be used both as such and after blocking with blocking agents for isocyanate groups such as ε-caprolactam, methyl ethyl ketone, malonic acid diethyl ester or acetoacetic acid ethyl ester. The new diisocyanate may of course also be used in admixture with other diisocyanates of the type known from polyurethane chemistry. By virtue of the very pronounced differences in reactivity between the two isocyanate groups, the asymmetrical diisocyanate according to the invention is also eminently suitable for the production of polyurethane plastics on the two-stage principle. In a first stage, prepolymers containing free isocyanate groups are initially prepared from the diisocyanate according to the invention and subequivalent quantities of organic polyhydroxyl compounds of the type known per se in polyurethane chemistry. The prepolymers are then converted into high molecular weight polyurethanes in a second stage using suitable chain-extending agents. Before it is used in the production of polyurethane plastics, the diisocyanate according to the invention may also be converted in known manner into a derivative containing isocyanurate, uretdione or biuret groups which, before it is further processed, may optionally be freed by distillation from unreacted excess diisocyanate.

The diisocyanate according to the invention or its modification products may be used in particular in the lacquer field, i.e. for the production of one-component and two-component polyurethane lacquers.

In the following examples, all of the percentages are percentages by weight.

COMPARISON EXAMPLE 1

Corresponds to Example 7 of DE-OS 1,618,798

113.2 g (1.0 mole) of ε-caprolactam and 1.0 mole concentrated aqueous hydrochloric acid were introduced into a 2-liter four-necked flask equipped with a gas inlet pipe and a reflux condenser. This solution was heated for 1 hour to reflux with the introduction of hydrogen chloride (at a rate of 0.5 mole/hour). 89.0 g (1.0 mole) 2-aminobutanol, which had been dissolved in 100 ml benzene, and 300 ml o-dichloro-benzene were then added over a period of 30 minutes. During the addition, the introduction of gaseous hydrogen chloride was increased to 1 mole per hour. The mixture was then further heated under reflux on an azeotropic separator with continuous introduction of a slow stream of hydrogen chloride. The reflux temperature was constant at 115° C. which necessitated the periodic addition of benzene. After a total of 16.5 hours under reflux, no water collected in the trap. This was an indication that the esterification reaction was over. However, exact analysis of the pasty, solid-liquid mixture thus obtained was not possible. An attempt to isolate some of the dihydrochloride by careful removal of the solvent resulted in decomposition of the product.

The mixture was phosgenated for 4 hours at 140° C. and then for another 2 hours at 150° C. using a stream of phosgene introduced at a rate of 2 moles/hour. The benzene, which passed over into the Dean-Stark trap, had to be removed to reach the required temperature.

The reaction product obtained was in the form of a tar-like mass from which the supernatant solvent including reaction product had to be decanted off. After removal of the solvent and distillation through a thin-layer column (250° C./0.7 mbar), a highly impure product (according to analysis by gas chromatography) was obtained in a yield of 21 g (approx. 10% of the theoretical).

COMPARISON EXAMPLE 2

Corresponds to Example 8 of DE-OS 1,618,798

6-isocyanatocaproic acid
(2-isocyanato-2-methylpropyl)-ester 113 g ε-caprolactam and 89 g 2-amino-2-methyl propanol and, gradually, 2.2 moles concentrated hydrochloric acid were introduced into a 2-liter four-necked flask equipped with a gas inlet pipe and reflux condenser. After 3 hours under reflux, most of the water was distilled off under reduced pressure. The temperature of the reaction mixture was kept below 85° C. during the distillation. 450 ml o-dichlorobenzene were then added, the mixture was heated to 115° C. and HCl gas was slowly introduced. Another 150 ml benzene were added and the final traces of water were azeotropically removed. Once again, only the absence of any further separation of water served as an indication that the reaction was over. Exact analysis of the extremely inhomogeneous reaction product was not possible. The benzene was then removed under reduced pressure and replaced by 100 ml o-dichlorobenzene. This mixture was then phosgenated for 4 hours at 130° C. and then for 2 hours at 140° C. (200 to 250 g/h phosgene). To remove excess phosgene, the clear reaction mixture was purged with nitrogen for 15 minutes, 500 ml anhydrous o-dichlorobenzene were added and the mixture was distilled at 80° to 90° C./15 mbar (approx. 500 ml distillate). The mixture was then cooled and a viscous mass (solid at room temperature) was separated. A few ml (according to gas chromatography) of the highly pure product could be separated from this mass by distillation.

COMPARISON EXAMPLE 3

Preparation of 6-isocyanatocaproic acid
(2-isocyanato-2-methyl-1-propyl)-ester by phosgenation
in a low-boiling solvent 92.2 g 2-amino-2-methyl propanol in 1000 ml methylene chloride were introduced into a 4-liter four-necked flask. This solution was then saturated with hydrogen chloride gas at 20° to 40° C., resulting in the formation of a suspension of 2-amino-2-methyl propanol hydrochloride. A solution of 186 g 6-amino-caproyl chloride hydrochloride in 660 ml methylene chloride (prepared in accordance with H. Ulrich et al, Liebigs Ann. der Chemie 1975, p. 1317) was then added to this mixture over a period of 50 minutes at a temperature of 20° C. A greasy deposit was formed. The temperature was then increased to 40° C. and the remaining hydrochloric acid driven out. Further purification or isolation of the dihydrochloride was not possible.

For solvent exchange, 1700 ml dichloroethane were added and methylene chloride was distilled off through a 0.5 m packed column. Direct production of the dihydrochloride in dichloroethane was not possible due to the poor solubility of 6-aminocaproyl chloride hydrochloride in this solvent.

After the addition of a few boiling stones, the diaminodihydrochloride thus obtained was heated to reflux with introduction with phosgene (50 g/h) in a 4-liter phosgenation apparatus. The initially viscous hydrochloride liquefied so that the reaction mixture could be stirred. The mixture was phosgenated under reflux (80° C.) for 26 hours, resulting in the formation of an almost clear solution. The excess phosgene was then removed by distillation and a small solids component separated off by filtration. The solution was then completely freed from dichloroethane by distillation. The brownish, crude isocyanate remaining behind was distilled in vacuo in 6 portions and 220 g of an almost colorless liquid were obtained. For redistillation, the product was redivided into 6 portions which were each distilled at 98°-102° C./0.1 mbar.

Total yield: 210.5 g=83% of the theoretical
Total distillation residues: 33.9 g
Colorless liquid,
NCO content: Calc. 33.0%, found 31.4%
Hydrolyzable chlorine: 0.45%

According to mass spectrometry, only about 78% of the product consisted of the required diisocyanate; further purification was not possible because further distillation of the mixture at approximately 100° C. resulted partly in a decomposition and, accordingly, had to be terminated.

EXAMPLE 4

6-aminocaproic acid (3-amino-2,2-dimethyl-1-propyl)-ester dihydrochloride 535 g (5.2 moles) 3-amino-2,2-dimethyl-1-propanol in 5 liters methylene chloride were introduced into a 10-liter reaction flask. This solution was then saturated with HCl gas at 20° to 40° C., resulting in the formation of a slightly cloudy solution of the corresponding neopentanol-amine hydrochloride. A solution of 930 g (5 moles) 6-aminocaproyl chloride hydrochloride in 3.3 liters methylene chloride (prepared in accordance with H. Ulrich et al, Liebigs Ann. d. Chemie 1975, pages 1317-1321) was then added dropwise to this mixture over a period of 2 hours at 20° C.

The hydrochloric acid formed was then driven off by heating to 40° C. The initially viscous deposit changed into a crystalline form and could be filtered under suction without difficulty. After drying at 50° C./100 mbar, 1420 g (98.3% of the theoretical) of the desired hydrochloride were obtained without further purification.

Melting point: 154° C.
$C_{11}H_{26}N_2O_2Cl_2$ (289) Found: C: 45.7%; H: 9.3%; N: 9.6%; Cl: 24.4%, Calculated: C: 45.7%; H: 9.0%; N: 9.7%; Cl: 24.5%.

EXAMPLE 5

6-isocyanatocaproic acid (3-isocyanato-2,2-dimethyl-1-propyl)-ester

A mixture of 289 g finely crystalline 6-amino-caproic acid-(3-amino-2,2-dimethyl-1-propyl)-ester dihydrochloride and 3.5 liter anhydrous chlorobenzene was introduced into a 6-liter laboratory phosgenation apparatus and rapidly heated with stirring to reflux. At the same time, phosgene was introduced into the suspension (approx. 50 g/h). The mixture was then phosgenated under reflux for 8 hours, resulting in the formation of a clear solution. The reaction mixture was then freed from excess phosgene and from chlorobenzene by distillation. The brownish colored liquid remaining behind was distilled in vacuo, 6-isocyanato-caproic acid (3-isocyanato-2,2-dimethyl-1-propyl)-ester being obtained in the form of a colorless liquid boiling at 134° to 138° C./0.1 mbar. The diisocyanate could be almost completely redistilled without significant residue formation.

$C_{13}H_{20}N_2O_4$ (268.3) Found: C: 58.1%; H: 7.6%; N: 10.5% Calculated: C: 58.1%; H: 7.5%; N: 10.4%
NCO-content: calculated 31.3%, found 31.3%
Yield: 252 g (94% of the theoretical)
Boiling point: 115° C./0.05 mbar.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a diisocyanate corresponding to the formula

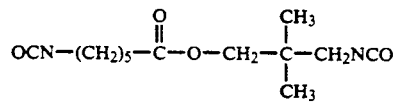

which comprises a) reacting the adduct of 3-amino-2,2-dimethyl-1-propanol and hydrogen chloride with 6-aminocaproyl chloride hydrochloride to form a diaminohydrochloride corresponding to the formula

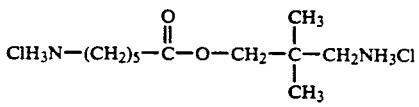

and b) subsequently reacting said diaminohydrochloride with phosgene to form said diisocyanate.

2. The process of claim 1 which comprises separating hydrogen chloride from said diaminohydrochloride and recovering said diaminohydro-chloride in crystalline form.

* * * * *